(12) United States Patent
Guru

(10) Patent No.: US 6,505,966 B1
(45) Date of Patent: Jan. 14, 2003

(54) METHOD AND APPARATUS FOR ASSESSING THE PERFORMANCE OF AN X-RAY IMAGING SYSTEM

(75) Inventor: Shankar Visvanathan Guru, Brookfield, WI (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 09/575,698

(22) Filed: Jul. 7, 2000

(51) Int. Cl.[7] .............................................. G01D 18/00
(52) U.S. Cl. ......................... 378/207; 378/18; 378/117
(58) Field of Search ........................... 378/207, 18, 117

(56) References Cited

U.S. PATENT DOCUMENTS

| | | | | |
|---|---|---|---|---|
| 4,991,193 A | * | 2/1991 | Cecil et al. .................. | 378/117 |
| 5,473,663 A | * | 12/1995 | Hsieh ........................... | 378/207 |
| 6,275,559 B1 | * | 8/2001 | Ramani et al. ................ | 378/4 |
| 6,359,955 B1 | * | 3/2002 | Nukui ............................ | 378/4 |

OTHER PUBLICATIONS

"Discrete–Time Control Systems", by Katsuhiko Ogata, Prentice–Hall, Inc., Chapter 7, pp. 867–883 (1987).

* cited by examiner

*Primary Examiner*—Drew A. Dunn
*Assistant Examiner*—Elizabeth Gemmell
(74) *Attorney, Agent, or Firm*—Donald S. Ingraham; Christian G. Cabou

(57) ABSTRACT

A method and apparatus are provided for assessing performance of an imaging system. The imaging system has a performance assessment apparatus that comprises a system performance computer configured to execute a performance assessment algorithm. The performance assessment computer is coupled to receive signals from the detector assembly of the imaging array in a plurality of imaging system operating modes so as to identify disparities between actual system performance and nominal system performance for respective ones of the imaging system operating modes and to provide respective system performance output signals. The method of the present invention for assessing performance of an imaging system includes the steps of collecting signals representative of detected radiation incident on the detector assembly of the imaging system; processing the detected radiation signals in accordance with a performance assessment algorithm so as to identify disparities between detected actual system performance and nominal system performance for a respective one of the imaging system operation modes; and generating a system performance output signal corresponding to the respective system operating mode.

39 Claims, 6 Drawing Sheets

METHOD AND APPARATUS FOR ASSESSING THE PERFORMANCE OF AN X-RAY IMAGING SYSTEM

BACKGROUND OF THE INVENTION

The invention generally relates to x-ray imaging systems, and more particularly to a method and apparatus for assessing performance of imaging systems such as computed tomography (CT) system based on a performance assessment algorithm comparing actual system operation with nominal calibration data.

Solid state imaging systems have been developed that employ an x-ray source (typically an x-ray tube); a detector assembly comprising radiation detectors (commonly having a scintillator coupled to a photosensor array or alternatively solid state radiation detectors); and read-out electronics coupled to the detector assembly to process electrical signals from the detector elements and provide an image for viewing or further processing. Desirably the operator of an imaging system is provided with periodic checks, such as with each system start up, that confirms nominal system performance or identifies areas of degraded performance.

Notification and identification of areas of substandard system performance is desirable to provide for prompt repair and return of the system to service. Prior prediction of areas of substandard system performance is desirable as it enable advance scheduling of "downtimes," which is extremely beneficial to the smooth functioning of hospitals or other imaging facilities. Further, it is desirable that such performance assessment checks be readily accomplished in the course of normal system operation, such as during system start up or during normal imaging operation.

Accordingly, a need exists for a method and apparatus that enable efficient and prompt assessment of imaging system performance.

SUMMARY OF THE INVENTION

The invention provides a method and apparatus for assessing performance of an imaging system. The imaging system has a performance assessment apparatus that comprises a system performance computer configured to execute a performance assessment algorithm. The performance assessment computer is coupled to receive signals from the detector assembly of the imaging array in a plurality of imaging system operating modes so as to identify disparities between actual system performance and nominal system performance for respective ones of the imaging system operating modes and to provide respective system performance output signals and prediction signals regarding system performance.

The method of the present invention for assessing performance of an imaging system includes the steps of collecting signals representative of detected radiation incident on the detector assembly of the imaging system; processing the detected radiation signals in accordance with a performance assessment algorithm so as to identify disparities between detected actual system performance and nominal system performance for a respective one of the imaging system operation modes; and generating a system performance output signal corresponding to the respective system operating mode.

DETAILED DESCRIPTION

The present invention provides means for assessing the performance of an x-ray imaging system 2. As used herein, "x-ray imaging system" and the like refer to a system for imaging objects with x-rays that employs radiation detectors as described herein. The radiation detector typically comprises a plurality of detector elements, as described more fully below for certain embodiments, that provide electrical signals representative of the detected incident x-ray radiation. These electrical signals from the respective detector elements are then processed to provide a representation of the image of the object being irradiated. Commonly the radiation detector comprises a scintillator coupled to a photosensor array, although alternative embodiments can employ. semiconductor devices for direct detection of incident radiation. By way of example, and not limitation, the apparatus and method of the present invention is described with respect to one embodiment in which it is used, that of a computed tomography ("CT") system.

Figure 1:
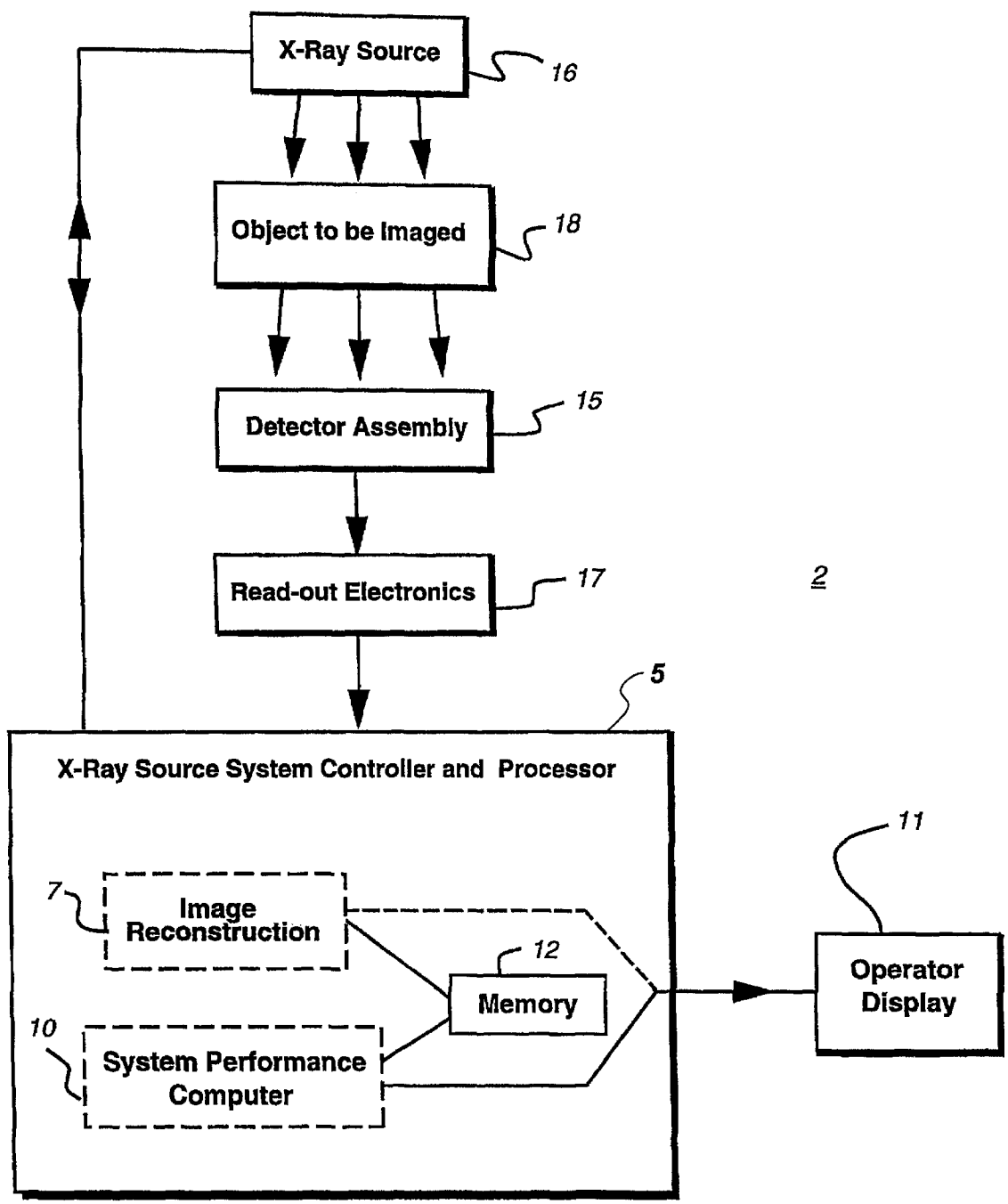
FIG. 1 is a block diagram of one embodiment of a radiation imaging system of the present invention.

FIG. 1 is a block diagram of a typical CT system 2 being used to image a patient 18. The CT system comprises various sub-systems for acquiring a CT image of the patient 18, for processing electrical signals associated with the image, and for displaying the CT image. The CT system comprises an x-ray source 16, which comprises an x-ray tube (not separately shown), a detector assembly 15 which comprises a plurality of detector elements (not separately shown in FIG. 1) that receives the x-rays that pass from x-ray source 16 and generate corresponding electrical signals. Read-out electronics 17 are coupled to detector assembly 15 to read the electrical signals, amplify the signals as necessary, and provide the electrical signals representative of the detected incident radiation to a system controller and processor 5 for processing of the signals.

Processor 5 comprises, e.g., an image reconstruction computer 7 configured to process the acquired image data signals to reconstruct a CT image and provide the reconstructed CT image to be displayed on the display monitor 11. Processor 5 further comprises a system performance computer 10 configured to execute a performance assessment algorithm as described below. As used herein, "configured to," "adapted to," and the like refer to processing devices such as programmable digital computers, application specific integrated circuits (ASICs), that manipulate input data signals in a manner to provide a desired output signal. The term "computer", as that term is used herein, is intended to denote any machine capable of performing the calculations, or computations, necessary to perform the manipulations of signals for generation of, e.g., outputs in steps of the performance assessment process of the invention. In essence, this includes any machine that is capable of accepting a structured input and of processing the input in accordance with prescribed rules to produce an output. Thus computer 10 is not limited to any particular physical, structural, or electrical configuration.

Processor 5 typically further comprises a memory device 12 that stores various programs and/or data utilized by the performance computer 10 and image reconstruction computer 7. Reference to image reconstruction computer 7 and system performance computer 10 is made for convenience in describing the apparatus of the present invention and does not necessarily imply that separate and distinct digital computing devices need to be used, but rather indicates that there is a digital computing device configured to execute the particular algorithms described herein.

Performance assessment computer 10 executes a performance assessment algorithm to identify disparities between detected actual system performance and nominal system performance. As used herein, "detected actual system performance" and the like refers to imaging system operation as evidenced by the imaging data signals generated by the system for a given operating condition. "Nominal system performance" and the like refers to a performance standard determined for machine operation, and represents a calculated or calibrated norm for such imaging operation (e.g., designed performance with a calibration standard such as a water phantom in place). Typically the performance assessment algorithm is implemented in software, which is executed by the computer 10; in alternative embodiments, however, the performance assessment algorithm may be implemented solely in hardware or in a combination of hardware and software.

Memory device 12 typically is utilized for storing the software that performs the performance assessment algorithm, for storing data utilized by and generated by the performance assessment algorithm. For example, historical performance data of the particular imager (or alternatively, a plurality of imagers of appropriate for comparison) may be used in generation of performance profiles and expected future performance.

Figure 2:
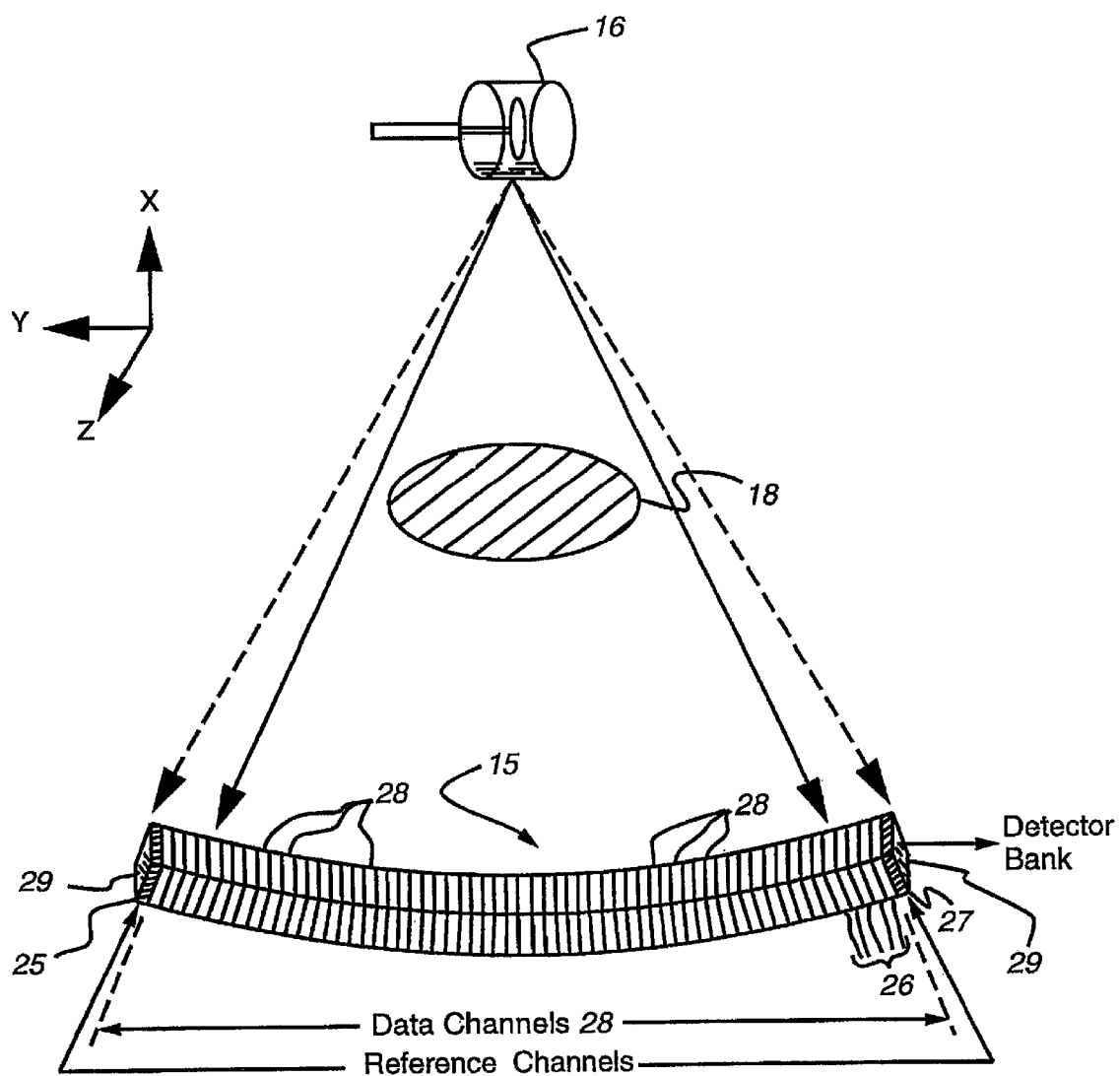
FIG. 2 is a drawing depicting one embodiment of the detector assembly adapted for use in accordance with the present invention.

Detector assembly 15 comprises a plurality of detector channels 26 ( a representative number of which are indicated in FIG. 2). Each detector channel 26 corresponds to at least one (and, alternatively, multiple) detector element 28, e.g., a photodiode or the like that is used to generate the electrical signals representative of radiation incident on a given portion (typically referred to as a pixel) of the detector assembly. In CT applications, it is common that multiple channels are bundled together in modules for ease of packaging (e.g., currently a typical CT detector assembly comprises 57 modules, each of which comprises 16 detector elements).

Detector channels 26 further comprise data channels 28 and at least one reference channel 25. The reference channel provides a signal indicative of detected x-rays that have not interacted with (e.g., have not been attenuated by passing through) object 18 that is being imaged. Thus, the reference channel provides a signal representative of x-ray flux generated by x-ray source 16. The data channels are disposed to receive radiation emanating from source 16 that passes through object 18 that is to be imaged. The data channels thus provide respective signals representative of the attenuation of the x-ray signal resulting from passage through object 18 to be imaged, which signals are processed for display of the image.

Detector assembly 15 in a CT system commonly comprises two reference detector elements 25 and 27, with associated respective reference channels 29 that provide the reference channel output signal. The reference detectors are typically disposed adjacent the ends of the detector assembly 15, as shown in FIG. 2. The reference detectors are disposed so as to receive x-rays directly from source 16 without the x-rays interacting with an object 18 that is imaged by the imager. Alternative locations for reference detectors are possible, given particular array designs and uses, so long as there is an uninterrupted path for x-rays to the reference detector for times when the reference detector is providing signals for a reference channel.

As noted above and illustrated in FIG. 2, the detector elements disposed between the reference detector elements comprise the data detector elements, which capture x-rays that pass through an object being imaged by the CT system.

Figure 3:
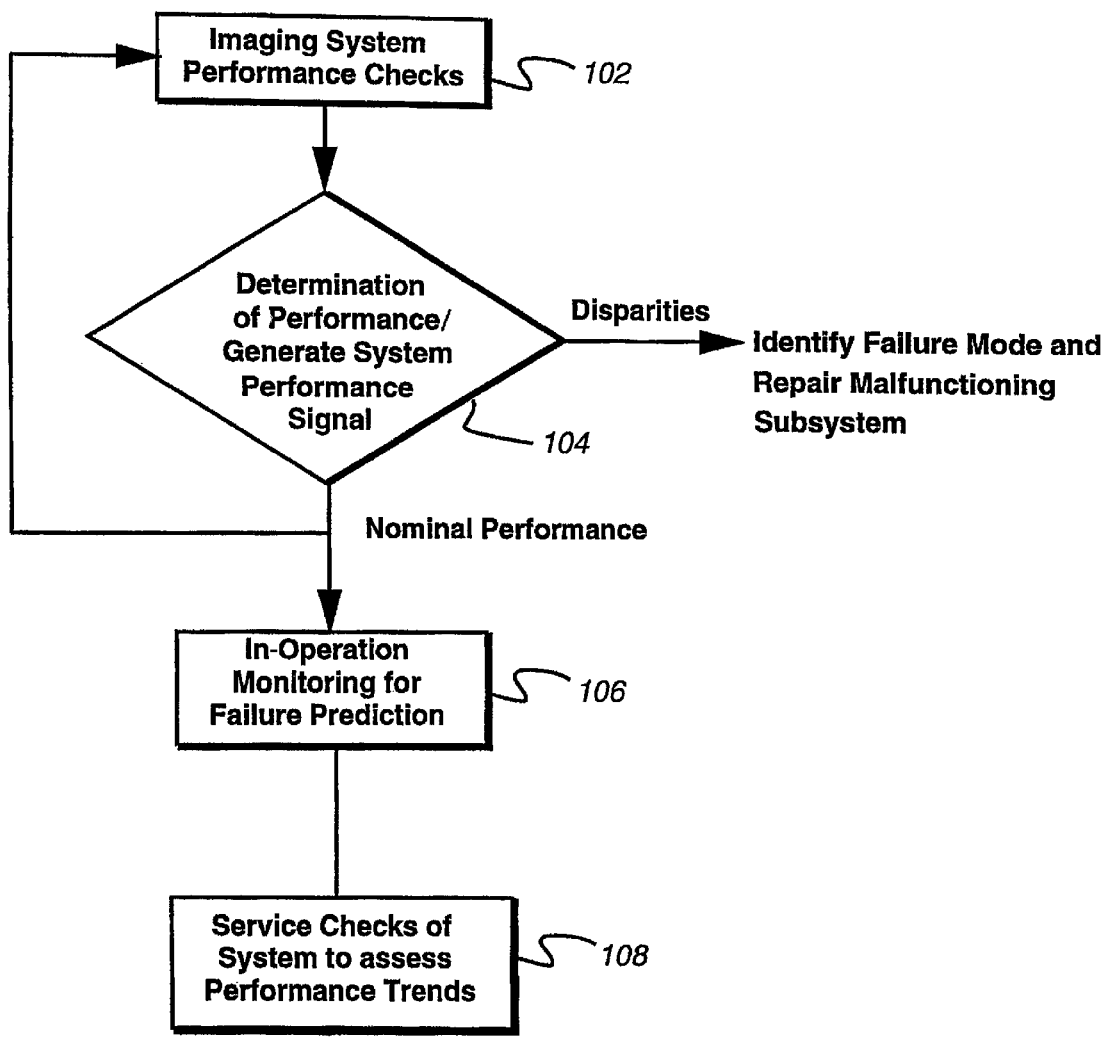
FIG. 3 is a flow chart generally illustrating the method of the invention for assessing performance of a radiation imaging system.

Assessment of the operation of radiation imaging system 2 in accordance with the apparatus and methods described herein is outlined in FIG. 3. System performance assessments include the step of conducting imaging system performance checks 102, as described in more detail below. Based upon processing of data obtained in a system performance check 102, a determination of system performance 104 is made and a system performance output signal is generated. Such performance checks generally involve checks conducted during normal system operation, such as start up operations, normal imaging operation, periodic calibration checks, or shut down operations. Typically, such a determination broadly is characterized as nominal performance, or alternatively identification of a disparity with nominal system performance.

In the event nominal system performance is determined, imaging system performance checks as described herein can be periodically conducted (as indicated by the loop-back line in FIG. 3 between box 104 and 102). Additional checks, such as monitoring for failure prediction 106, can be performed; one example of such a process is described in copending application Ser. No. 09/575,699, now U.S. Pat. No. 6,351,517, filed contemporaneously herewith, entitled "Method and Apparatus for Predicting X-ray Tube Failures in Imaging Systems." Failure prediction monitoring generally provides a projection of impending component failure based upon analysis of operational data reflecting that component's present and historical performance. Further monitoring of the imaging system 2 can comprise periodic service checks 108 of the system to assess performance trends (e.g., involving installation or activation of special test equipment and the like); as used herein, such periodic service checks are performed by service technicians other than during normal operations.

Figure 4:
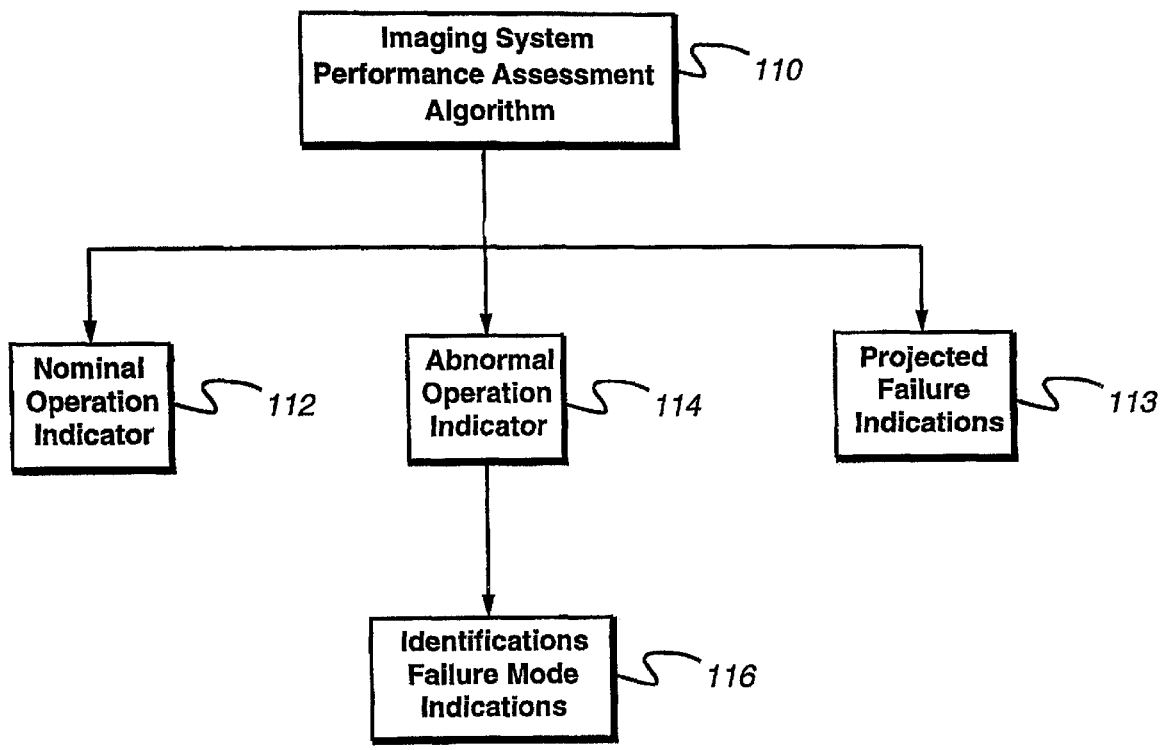
FIG. 4 is a block diagram depicting further details of one embodiment of the performance assessment algorithm for generating a system performance signal of the present invention.

In one embodiment of the present invention, system performance computer 10 is configured to execute a performance assessment algorithm 110 (FIG. 4) for a number of operating modes of the imaging system. The system performance computer generates a system performance output signal that characterizes analyzed system performance, such as nominal system performance indications 112; abnormal (i.e., other than nominal performance) system operation indications 114; failure mode identification indications 116 (in the event of detected abnormal system operation); and projected failure indications 116. The system performance algorithm typically incorporates a plurality of prediction algorithms that employ analysis tools, such as for example, Kalman filters adapted for use with particular data set manipulations.

One operating mode is referred to herein as an "imaging system check operating condition," which refers to a check routine that is used to provide an assessment of detector performance and tube performance. Such a check is commonly used in the startup sequence, but also can be conducted between patient imaging operations if desired by the operator.

Figure 5:
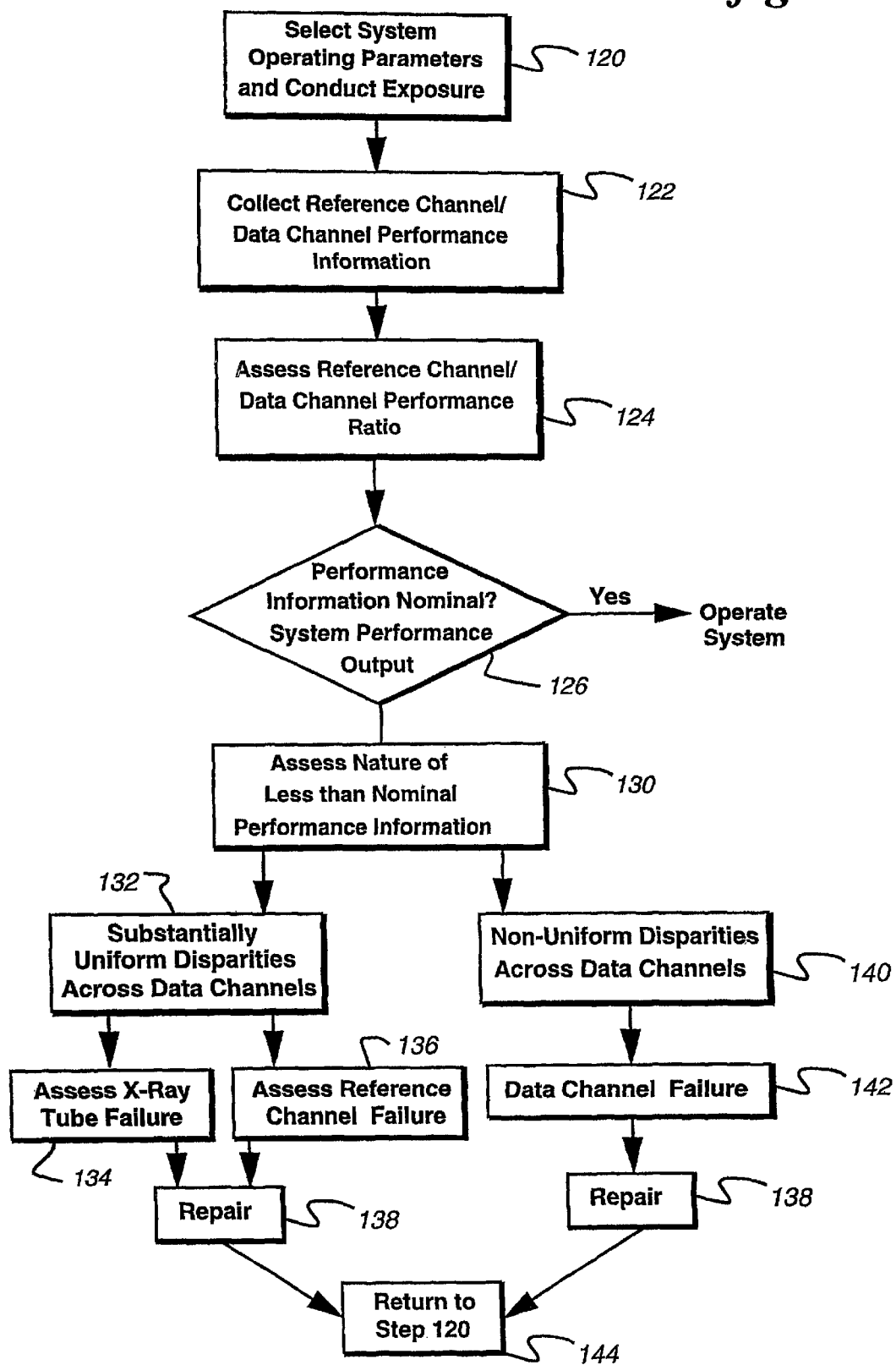
FIG. 5 is a flow chart illustrating one aspect of the performance assessment algorithm of the present invention.

As outlined in the flow chart of FIG. 5, the imaging system check operating condition routine typically begins with selection of imaging system operation parameters 120 (e.g., selection of tube power parameters (e.g., filament, target, KvP, mAs, filter tube selection, collimator setting) and energizing x-ray source 16 to conduct exposures. Once the operating parameters are set, exposures are conducted to collect reference channel and data channel performance information 122. Such exposures typically includes imaging a water phantom, or other object of known size and radiation attenuation characteristics, or exposure of the detector assembly 15 without an object disposed to be imaged. Exposure data is collected at step 122 for the above-described exposure routines, including reference channel readings and respective data channel performance information (e.g., the x-ray flux detected at respective detector elements).

One aspect of the imaging system check operation condition routine is the determination of a "performance ratio" (in step 124) of respective detector data channel outputs to at least one of the reference channel outputs. The performance ratio represents a correlation between the x-ray flux signals generated at respective detector data channels and the x-ray flux signal generated by one (or multiple reference channels). By way of example and not limitation, one means of expressing the mathematical relationship between the two respective flux signal values is to divide the reference channel signal by the detector channel signal, with the quotient of this division providing the performance ratio for a respective data channel.

For example, in the arrangement in which a known water phantom is imaged, the ratio of reference channel signal values to data channel signal values provides information that is useful in assessing imaging system performance. The performance ratio is typically compared to a predetermined calibration reference in step 126; if system performance is nominal, the operator proceeds with operation of the imaging system. If an abnormality is detected, the performance assessment algorithm proceeds to assess the nature of the less than nominal system performance in step 130. The calibration reference for the performance ratio can be a measured standard for a particular detector under known conditions (e.g., at manufacture or in a service mode) or can represent a design projection for imager performance).

Figure 6:
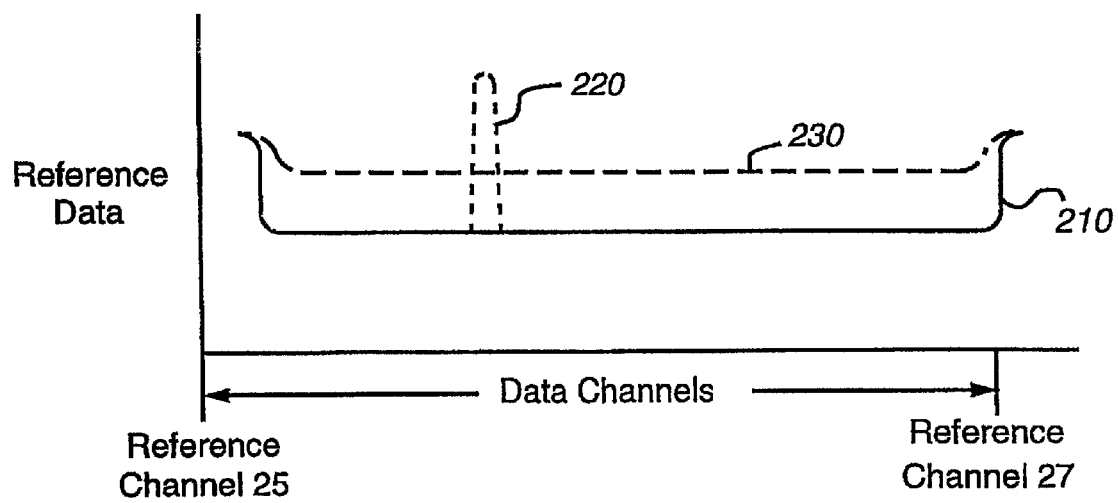
FIG. 6 is a chart providing illustrative performance ratio information as generated in the present invention.

One example of the performance ratio assessment is shown in FIG. 6. Curve 210 represents nominal performance of the system; that is the detected actual performance corresponds with the predetermined calibration reference ("corresponds to," as used in this context, implies conformance within a defined specification for variation, which specification is typically determined by the manufacturer of the particular device). In other words, each data channel is providing an x-ray flux signal that represents the attenuation of x-rays corresponding to the presence of the known object to be imaged (e.g., water phantom, which desirably provides a uniform attenuation across all data channels). A non-uniform variation (step 140) in the performance ratio across the data channels, such as the spike in the performance ratio curve illustrated by the dotted line curve 220 in FIG. 6, is indicative of data channel failure (step 142). A substantially uniform disparity between the performance ratio and the calibration reference (step 132), for example as illustrated by curve 230 in FIG. 6, is indicative of either an x-ray tube malfunction (step 134) (that is, the overall x-ray flux is at variance with what it should be given the parameters set in step 120), or is indicative of a reference channel failure (step 136). Further diagnostic tests (typically involving special service tests of the unit) are necessary to identify which of these two failure modalities has occurred. Regardless of the failure mode identified, repair of the imager system is undertaken in step 138 to correct the malfunction, and, upon system restart after repair, the performance assessment routine for the check operating condition is conducted again, as indicated in step 144.

By way of example and not limitation, uniform disparities between the detected actual performance ratio values and the calibration reference values can be resolved with further examinations to assess x-ray tube performance. The condition of the x-ray tube 16 can be determined in a plurality of manners, such as, for example, an ionization chamber (not shown) can be used to determine whether or not the x-ray tube 16 is operational.

The system performance signal generated at step 104 is typically presented to the operator. Such notification may be displayed on the display monitor 11 or it may be displayed on a separate display monitor (not shown) connected to the computer 10, or sent to other diagnostic system equipment either on site or at a remote site. Alternatively, the notification may be provided in printed format by printing the notification on a printer (not shown) connected to computer 10.

Similarly, predictions of system performance can also be made based upon system performance assessment and models of system performance (as described, for example, for the x-ray tube condition copending case Ser. No. 09/575, 699, now U.S. Pat. No. 6,351,517, cited above and incorporated herein by reference.

It should be noted that the invention has been described with reference to the the embodiments described above, but that the invention is not limited to these embodiments. For example, although the invention has been discussed with reference to a detector in which the detector elements and the read-out electronics are integrated into the detector array, those skilled in the art will understand that the invention is not limited with respect to the type of detector array utilized in the imaging system.

Those skilled in the art will also understand that the invention is not limited with respect to the manner in which the detector array and the x-ray tube are checked to determine whether they are functioning prior to the performance assessment routines being performed. Those skilled in the art will understand that other modifications may be made to the embodiments discussed herein that are within the scope of the invention.

What is claimed is:

1. An x-ray imaging system having a performance assessment apparatus for assessing performance of the imaging system, the imaging sub-systems comprising an x-ray source, an x-ray detector assembly having a plurality of detector elements, and read-out electronics coupled to the detector elements, the performance assessment apparatus comprising:

a system performance computer configured to execute a performance assessment algorithm, the computer being coupled to said detector assembly to receive signals therefrom; said signals including signals from data channels and from at least one reference channel in said detector assembly, said performance assessment algorithm further comprising models of nominal system performance relating data between said at least one reference channel and at least one data channel, said computer further being configured to process signals received from said detector in a plurality of imaging system operating modes so as to identify disparities between detected actual system performance and nominal system performance for a respective one of said imaging system operating modes and to provide a respective system performance output signal.

2. The imaging system of claim 1 wherein said system performance output signal comprises nominal system operation indications, abnormal system operation indications, failure mode identification indications, and projected failure indications.

3. The imaging system of claim 2 wherein said system performance computer is configured to provide a system performance signal in correspondence with an imaging system check operating condition.

4. The imaging system of claim 2 wherein said system performance computer is configured to provide an in-operation x-ray tube failure prediction signal in correspondence with a system imaging operating condition.

5. The imaging system of claim 2 wherein each of said at least one reference channel and said plurality of data channels correspond to at least one of said detector elements, said at least one reference element being disposed in said detector so as to receive x-ray radiation directly from said x-ray source without said radiation impinging on intermediate objects.

6. The imaging system of claim 5 wherein said system performance computer is configured to provide a system performance signal in correspondence with an imaging system check operating condition, said imaging system check operating condition corresponding to a performance ratio of respective detector data channel outputs to said at least one reference channel output, said performance ratio corresponding to the quotient of the at least one reference channel signal to respective ones of the data channel signals, said data channel signals being representative of radiation detected at respective ones of said detector elements with a reference phantom object disposed in said imaging system to be imaged.

7. The imaging system of claim 6 wherein said system performance computer is further configured to compare said performance ratio to a predetermined calibration reference for said detector assembly.

8. The imaging system of claim 7 wherein said system performance computer is further configured to characterize the comparison between said performance ratio and said predetermined calibration reference for said detector assembly as nominal, uniform disparities, and non-uniform disparities.

9. The imaging system of claim 8 wherein said system performance computer generates a system performance signal indicative of a data channel failure when the comparison between said performance ratio and said predetermined calibration reference for said detector assembly is characterized as non-uniform disparities.

10. The imaging system of claim 9 wherein said system performance computer generates a system performance signal indicative of alternatively a x-ray tube failure or a reference channel failure when the comparison between said performance ratio and said predetermined calibration reference for said detector assembly is characterized as uniform disparities.

11. A method for assessing performance of an x-ray imaging system, the sub-systems including an x-ray tube, a detector assembly having a plurality of detector channels, said detector channels comprising at least one reference channel and a plurality of data channels, each detector channel corresponding to at least one detector element, and read-out electronics coupled to the detector elements, the method comprising the steps of:

collecting signals representative of detected radiation incident on said detector assembly in at least one of a plurality of imaging system operating modes;

processing the detected radiation signals in accordance with a performance assessment algorithm so as to identify disparities between detected actual system performance and nominal system performance for a respective one of said imaging system operating modes; said performance assessment algorithm further comprising models of nominal system performance relating data between said at least one reference channel and at least one data channel, and generating a system performance output signal corresponding to the respective system operating mode.

12. The method of claim 11 wherein said system performance output signal comprises nominal system operation indications, abnormal system operation indications, failure mode indications, and projected failure indications.

13. The method of claim 12 wherein the step of generating said system performance output signal comprises generating an in-operation x-ray tube failure prediction in correspondence with normal imaging system operations.

14. The method of claim 12 wherein the step of collecting signals representative of detected radiation comprises the steps of receiving channel signals for at least one reference channel in said detector assembly and for a plurality of data channels in said detector assembly.

15. The method of claim 14 wherein the step of processing the detected radiation signals in accordance with a performance assessment algorithm comprises the step of generating a performance ratio of respective detector data channel outputs to said at least one reference channel output, said performance ratio corresponding to the quotient of the at least one reference channel signal to respective ones of the data channel signals.

16. The method of claim 15 wherein said processing step further comprises comparing said performance ratio to a predetermined performance standard.

17. The method of claim 16 wherein, for a imaging system check operating condition, said step of comparing said performance ratio to a predetermined performance standard further comprises characterizing the comparison as nominal, uniform disparities, and non-uniform disparities.

18. The method of claim 17 wherein the step of generating a system performance output signal provides a signal corresponding to a data channel failure when the characterization of said comparison of said performance ratio to said predetermined performance standard corresponds to a non-uniform disparity.

19. The method of claim 17 wherein the step of generating a system performance output signal provides a signal corresponding to alternatively an x-ray tube failure or a reference channel failure when the characterization of said comparison of said performance ratio to said predetermined performance standard corresponds to a uniform disparity.

20. The method of claim 15 wherein a reference phantom object is disposed in said imaging system prior to collection of said data channel signals.

21. A computer program for assessing performance in a radiation imaging system, the imaging system having sub-systems including an x-ray tube, a detector assembly comprising a plurality of detector channels, and read-out electronics comprised coupled to the detector elements, the computer program being embodied on a computer-readable medium, the program comprising:

a first code segment for processing detector channel signals, the detector channel signals corresponding detected radiation impinging on said detector assembly, said detector channel signals comprising at least one reference channel and a plurality of data channels; and a second code segment, the second code segment processing the detector channel signals in accordance with a performance assessment algorithm so as to identify disparities between detected actual imaging system performance and nominal system performance for a respective one of a plurality of imaging system operating modes and to provide a respective system performance output signal, said performance assessment algorithm further comprising models of nominal imaging system performance relating data between said at least one reference channel and at least one data channel.

22. The computer program of claim 21 wherein said respective system performance output signal comprises nominal system operation indications, abnormal system operation conditions, failure mode indications, and projected failure indications.

23. The computer program of claim 21 wherein said code segment comprises an imaging system check operating condition sub-routine code segment.

24. The computer program of claim 23 wherein said detector channels comprise at least one reference channel and a plurality of data channels, each of said channels corresponding to at least one detector element, the detector element for said at least one reference channel being disposed so as to receive x-ray radiation directly from said x-ray tube without said radiation impinging on intermediate objects, the signal from each of said detector channels being processed by said first code segment and provided to said second code segment.

25. The computer program of claim 24 wherein said imaging system check operating condition sub-routine code segment generates a performance ratio of respective detector data channel outputs to said at least one reference channel output, said performance ratio corresponding to the quotient of the at least one reference channel signal to respective ones of the data channel signals, said data channel signals being representative of radiation detected at respective ones of said detector elements with a reference phantom object disposed in said imaging system to be imaged.

26. The computer program of claim 25 wherein said imaging system check operating condition sub-routine code segment further compares said performance ratio with a predetermined calibration reference.

27. The computer program of claim 26 wherein said imaging system check operating condition sub-routine code segment further characterizes the comparison between said performance ratio and said predetermined calibration reference for said detector assembly as nominal, uniform disparities, and non-uniform disparities.

28. The computer program of claim 27 wherein said imaging system check operating condition sub-routine code segment further generates a system performance signal indicative of a data channel failure when the comparison between said performance ratio and said predetermined calibration reference for said detector assembly is characterized as non-uniform disparities.

29. The computer program of claim 28 wherein said imaging system check operating condition sub-routine code segment further generates a system performance signal indicative of alternatively a x-ray tube failure or a reference channel failure when the comparison between said performance ratio and said predetermined calibration reference for said detector assembly is characterized as uniform disparities.

30. A computed tomography (CT) system comprising:

an x-ray source, the x-ray source comprising an x-ray tube that emits x-rays when energized;

an x-ray detector assembly, the detector assembly comprising a plurality of detector channels, each of the detector channels comprising at least one detector element, the detector elements being disposed in an array having at least one reference channel and a plurality of data channels, the respective detector element for said reference channel being disposed such that x-rays passing from said x-ray source impinge directly on said reference element without first interacting with objects to be imaged or components of said imager;

read-out electronics coupled to said detector elements, the read-out electronics reading the electrical signals generated by the detector channels; and a performance assessment apparatus, said apparatus being coupled to said read-out electronics and further comprising a system performance computer configured to execute a performance assessment algorithm in correspondence with signals generated by said detector channels in a plurality of operating modes so as to identify disparities between detected actual system performance and nominal system performance for a respective one of said imaging system operating modes and provide a respective system performance output signal, said performance assessment algorithm further comprising models of nominal system performance relating data between said at least one reference channel and at least one data channel.

31. The CT system of claim 30, wherein said system performance output signal comprises nominal system indications, abnormal system operation indications, failure mode identification indications, and projected failure indications.

32. The CT system of claim 30, wherein said system performance computer is configured to provide a system performance signal for an imaging system check operating condition routine.

33. The CT system of claim 32, wherein said system performance computer is configured to provide a system performance signal in correspondence with said imaging system check operating condition, said imaging system check operating condition corresponding to a performance ratio of respective detector data channel outputs to said at least one reference channel output, said performance ratio corresponding to the respective quotients of the at least one reference channel signal to respective ones of the data channel signals, said data channel signals being representative of radiation detected at respective ones of said detector elements with a reference phantom object disposed in said imaging system to be imaged.

34. The CT system of claim 33, wherein said system performance computer is further configured to compare said performance ratio quotients to a predetermined calibration reference representing nominal performance for said detector assembly.

35. The CT system of claim 34 wherein said system performance computer is further configured to characterize the comparison between said performance ratio and said predetermined calibration reference for said detector assembly as nominal, uniform disparities, and non-uniform disparities.

36. The CT system of claim 35 wherein said system performance computer generates a system performance signal indicative of a data channel failure when the comparison between said performance ratio and said predetermined calibration reference for said detector assembly is characterized as non-uniform disparities.

37. The CT system of claim 36 wherein said system performance computer generates a system performance signal indicative of alternatively a x-ray tube failure or a reference channel failure when the comparison between said performance ratio and said predetermined calibration reference for said detector assembly is characterized as uniform disparities.

38. The CT system of claim 30 wherein said reference channel detector element is disposed at one end of said detector assembly.

39. The CT system of claim 38 wherein said detector assembly comprises a first reference detector element disposed at one end of said detector assembly and a second reference detector element disposed at the opposite end of said detector assembly.

* * * * *